US011596352B2

(12) United States Patent
Takahashi

(10) Patent No.: US 11,596,352 B2
(45) Date of Patent: Mar. 7, 2023

(54) ROUTE SELECTION ASSISTANCE SYSTEM, RECORDING MEDIUM ON WHICH ROUTE SELECTION ASSISTANCE PROGRAM IS RECORDED, ROUTE SELECTION ASSISTANCE METHOD, AND DIAGNOSIS METHOD

(71) Applicant: TERUMO KABUSHIKI KAISHA, Tokyo (JP)

(72) Inventor: Haruhiko Takahashi, Shinagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 251 days.

(21) Appl. No.: 16/695,250

(22) Filed: Nov. 26, 2019

(65) Prior Publication Data

US 2020/0093421 A1  Mar. 26, 2020

Related U.S. Application Data

(63) Continuation of application No. PCT/JP2018/020530, filed on May 29, 2018.

(30) Foreign Application Priority Data

Jun. 2, 2017 (JP) .............................. JP2017-110378

(51) Int. Cl.
*A61B 5/00* (2006.01)
*A61B 5/107* (2006.01)
(Continued)

(52) U.S. Cl.
CPC ............ *A61B 5/489* (2013.01); *A61B 5/1075* (2013.01); *G06T 7/0012* (2013.01);
(Continued)

(58) Field of Classification Search
CPC ..... A61B 5/489; A61B 5/1075; G06T 7/0012; G06T 19/003; G06T 2207/30048; G06T 2207/30101; G06T 2210/41
See application file for complete search history.

(56) References Cited

U.S. PATENT DOCUMENTS

| 2008/0097165 A1 | 4/2008 | Gattani et al. |
| 2008/0183073 A1 | 7/2008 | Higgins et al. |
(Continued)

FOREIGN PATENT DOCUMENTS

| CN | 102871729 A | 1/2013 |
| CN | 103458764 A | 12/2013 |
(Continued)

OTHER PUBLICATIONS

The extended European Search Report dated Feb. 5, 2021, by the European Patent Office in corresponding European Patent Application No. 18810020.0-1122. (12 pages).
(Continued)

*Primary Examiner* — Vu Le
*Assistant Examiner* — Julius Chai
(74) *Attorney, Agent, or Firm* — Buchanan Ingersoll & Rooney PC

(57) ABSTRACT

A route selection assistance system enabling easy selection of a route of a living body lumen for delivering a medical instrument to a site within a living body via the living body lumen, a recording medium on which a route selection assistance program is recorded, and a route selection assistance method are disclosed. The route selection assistance system includes: a receiving section configured to receive an input of site information specifying a target site; an image obtaining section configured to obtain image information on a living body of a target patient; a route extracting section configured to extract a plurality of routes of a living body
(Continued)

lumen; a ranking assigning section configured to assign rankings to the plurality of routes according to ease of delivery of the medical instrument and patient scores determined according to magnitude of a burden imposed on the target patient.

17 Claims, 15 Drawing Sheets

(51) Int. Cl.
*G06T 7/00* (2017.01)
*G06T 19/00* (2011.01)

(52) U.S. Cl.
CPC .. *G06T 19/003* (2013.01); *G06T 2207/30048* (2013.01); *G06T 2207/30101* (2013.01); *G06T 2210/41* (2013.01)

(56) References Cited

U.S. PATENT DOCUMENTS

| | | | |
|---|---|---|---|
| 2008/0234700 | A1 | 9/2008 | Trovato et al. |
| 2009/0279767 | A1* | 11/2009 | Kukuk ............... G06T 7/74 382/132 |
| 2010/0008555 | A1 | 1/2010 | Trumer et al. |
| 2012/0296620 | A1 | 11/2012 | Aulbach |
| 2014/0039306 | A1 | 2/2014 | Klinder et al. |
| 2014/0088416 | A1 | 3/2014 | Sakuragi |
| 2014/0282216 | A1 | 9/2014 | Baker |
| 2014/0282261 | A1 | 9/2014 | Ranz et al. |
| 2015/0282887 | A1 | 10/2015 | Yamada |
| 2016/0070436 | A1 | 3/2016 | Thomas et al. |
| 2018/0085167 | A1* | 3/2018 | Goyal ............... A61B 34/00 |

FOREIGN PATENT DOCUMENTS

| | | |
|---|---|---|
| CN | 104050313 A | 9/2014 |
| EP | 3 144 834 A1 | 3/2017 |
| JP | 2000-113086 A | 4/2000 |
| JP | 2003-030624 A | 1/2003 |
| JP | 2009-511155 A | 3/2009 |
| JP | 2010-517633 A | 5/2010 |
| JP | 2014064824 A | 4/2014 |
| JP | 2014-124218 A | 7/2014 |
| JP | 2014180546 A | 9/2014 |
| JP | 2014230710 A | 12/2014 |
| JP | 2016-517288 A | 6/2016 |
| WO | 97/31581 A1 | 9/1997 |

OTHER PUBLICATIONS

International Search Report (PCT/ISA/210) dated Jul. 31, 2018, by the Japan Patent Office as the International Searching Authority for International Application No. PCT/JP2018/020530.

Written Opinion (PCT/ISA/237) dated Jul. 31, 2018, by the Japan Patent Office as the International Searching Authority for International Application No. PCT/JP2018/020530.

Office Action (Notice of Reasons for Refusal) dated Jun. 14, 2022, by the Japanese Patent Office in corresponding Japanese Patent Application No. 2019-521231 and an English Translation of the Office Action. (4 pages).

English translation of The First Office Action dated Sep. 26, 2022, by the State Intellectual Property Office of People's Republic of China in corresponding Chinese Patent Application No. 201880032097.0. (9 pages).

* cited by examiner

| INTRODUCTION SITE | INVASION DEGREE |
|---|---|
| RIGHT RADIAL ARTERY | LOW |
| RIGHT BRACHIAL ARTERY | MEDIUM |
| RIGHT FEMORAL ARTERY | HIGH |
| LEFT RADIAL ARTERY | LOW |
| LEFT BRACHIAL ARTERY | MEDIUM |

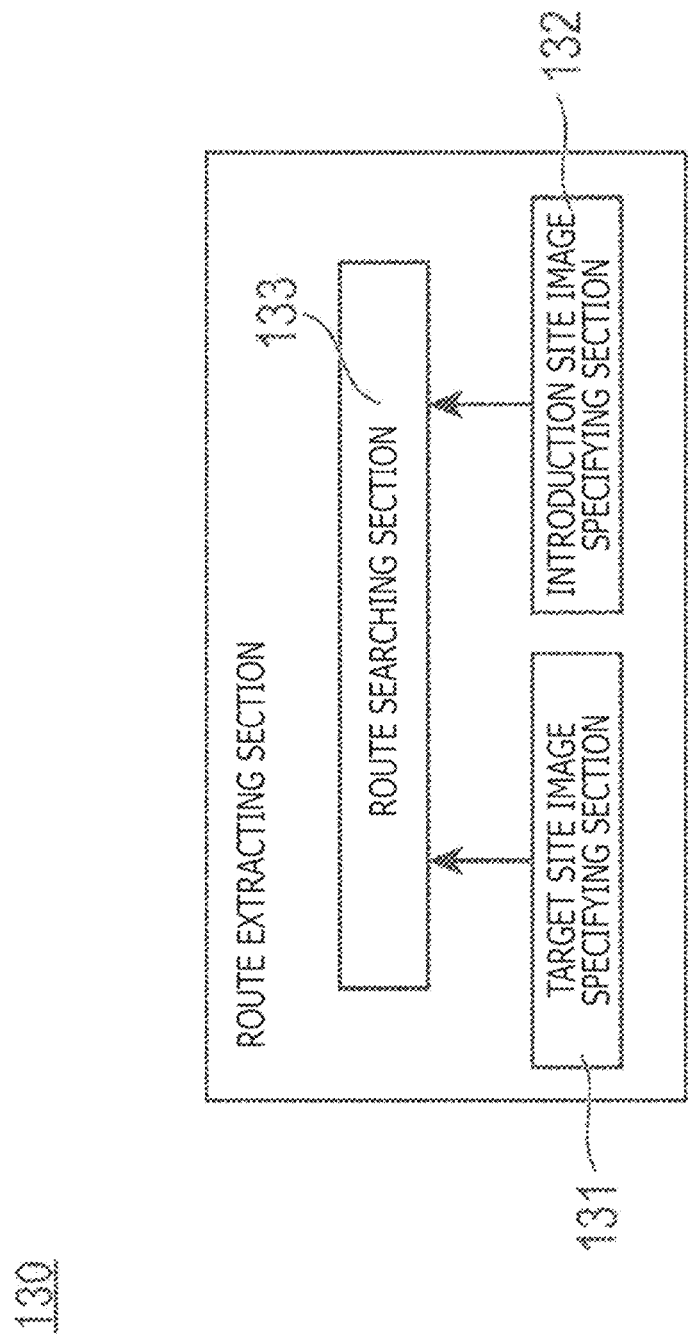

```
┌─────────────────────────────────────────────────────┐
│ PROCEDURE INFORMATION INPUT SCREEN                  │
├─────────────────────────────────────────────────────┤
│                                                     │
│                                                     │
│                       ┌──────────────────────┐      │
│   KIND OF PROCEDURE   │ EXPANSION OF      ▼  │      │
│                       │ CONSTRICTION         │      │
│                       └──────────────────────┘      │
│                                                     │
│                                                     │
└─────────────────────────────────────────────────────┘
```

| KIND OF PROCEDURE | KIND OF MEDICAL INSTRUMENT | | |
|---|---|---|---|
| PROCEDURE 1 | MEDICAL INSTRUMENT 1A | MEDICAL INSTRUMENT 1B | MEDICAL INSTRUMEN |
| PROCEDURE 2 | MEDICAL INSTRUMENT 2A | MEDICAL INSTRUMENT 2B | MEDICAL INSTRUMENT |
| PROCEDURE 3 | MEDICAL INSTRUMENT 3A | | |

| MEDICAL INSTRUMENT | DEVICE | | |
|---|---|---|---|
| MEDICAL INSTRUMENT 1A | DEVICE 1Aa | DEVICE 1Ab | DEVICE 1Ac |
| MEDICAL INSTRUMENT 1B | DEVICE 1Ba | DEVICE 1Bb | DEVICE 1Bc |
| MEDICAL INSTRUMENT 2A | DEVICE 2Aa | DEVICE 2Ab | DEVICE 2Ac |

| DEVICE | PRESENCE OR ABSENCE OF STOCK |
|---|---|
| DEVICE 1Aa | PRESENT |
| DEVICE 1Ab | ABSENT |
| DEVICE 2Ba | PRESENT |
| DEVICE 2Bb | |

ROUTE SELECTION ASSISTANCE SYSTEM, RECORDING MEDIUM ON WHICH ROUTE SELECTION ASSISTANCE PROGRAM IS RECORDED, ROUTE SELECTION ASSISTANCE METHOD, AND DIAGNOSIS METHOD

CROSS-REFERENCES TO RELATED APPLICATIONS

This application is a continuation of International Application No. PCT/JP2018/020530 filed on May 29, 2018, which claims priority to Japanese Application No. 2017-110378 filed on Jun. 2, 2017, the entire content of both of which is incorporated herein by reference.

TECHNICAL FIELD

The present disclosure relates to a route selection assistance system assisting in selecting a route of a living body lumen for delivering a medical instrument to a site within a living body via the living body lumen, a recording medium on which a route selection assistance program is recorded, a route selection assistance method, and a diagnosis method.

BACKGROUND ART

Procedures are known which perform treatment (for example, expansion of a constriction of a blood vessel), examination (for example, imaging of an inside region of a blood vessel), by delivering a medical instrument to a site within a living body via the blood vessel (living body lumen) (see JP 2014-230710A, for example).

The medical instrument can be introduced from the outside of the living body via a site as an access point to the blood vessel (which site will hereinafter be an introduction site) into the blood vessel, and is delivered to a target site as a target of the procedure via a plurality of sites of the blood vessel. For example, in a case where a blood vessel of a lower limb is treated by using trans radial intervention (TRI), the medical instrument can be introduced from a radial artery into the blood vessel, and delivered to the target site of the lower limb via an aortic arch, an aorta (descending aorta), and an iliac artery. TRI is a procedure that has recently been performed because of a relatively small burden on a patient as compared with trans femoral intervention (TFI) that introduces a medical instrument from a femoral artery.

There are a plurality of routes of blood vessels leading from the introduction site to the target site depending on the introduction site. An operator, for example, a doctor needs to select an appropriate route in consideration of the relative ease of delivery of a medical instrument at a time of delivery of the medical instrument, a relative burden on the patient, and the like. The relative ease of delivery of the medical instrument changes, for example, according to the magnitude of bending and curvature of sites of the blood vessel constituting a route.

However, the magnitude of bending and curvature of sites of the blood vessel differs for each target patient. Before starting the above-described procedure, the operator can check the magnitude of bending and curvature of sites of the blood vessel by visually recognizing an image of the inside of the living body of the target patient, and selecting an appropriate blood vessel route, which can depend on the experience of the operator, which can be a relatively great burden on the operator.

In a case of performing treatment of the blood vessel of a lower limb using TRI, for example, the number of sites of the blood vessel to be passed is increased as compared with TFI.

In TFI, when a retrograde puncture is performed from an ipsilateral femoral artery, the femoral artery and an iliac artery as a target of treatment are reached, and when a crossover approach can be performed from a contralateral femoral artery, an aortailiac bifurcation is passed from the femoral artery and an iliac artery, and an iliac artery or a femoral artery on an opposite side can be reached.

On the other hand, in performing treatment of a blood vessel of a lower limb from TRI, at a time of insertion from a right radial artery, an aortic arch is generally passed from the right radial artery, a right brachial artery, a right axillary artery, a right subclavian artery, and a brachiocephalic artery. At a time of insertion from a left radial artery, the aortic arch is generally passed from the left radial artery, a left brachial artery, a left axillary artery, the right subclavian artery, and the brachiocephalic artery. After the aortic arch is reached, a thoracic aorta and an abdominal aorta (descending aorta) are passed, and the aortailiac bifurcation can be reached.

Further reached to treat a lower limb artery are left or right one of common iliac arteries, external iliac arteries, internal iliac arteries, common femoral arteries, superficial femoral arteries, and deep femoral arteries, and further, as required, popliteal arteries, anterior tibial arteries, posterior tibial arteries, peroneal arteries, dorsalis pedis arteries, plantar arteries, and other arteries of the lower limbs, and peripheral blood vessels connected to arteries of the lower limb.

The magnitude of bending and curvature of sites of these blood vessels differs greatly for each target patient depending, for example, on age and a medical history. Further, in TRI, the blood vessel of the introduction site is relatively thin as compared with a brachial artery puncture and TFI, and the radial arteries are muscular arteries and thus tend to cause spasm (angiospasm). Therefore, in the case of performing treatment of the blood vessel of a lower limb or the like by using TRI, there is a particularly great burden of the work of selecting the route of an appropriate blood vessel as described above.

SUMMARY

A route selection assistance system is disclosed, which enables relatively easy selection of a route of a living body lumen for delivering a medical instrument to a site within a living body via the living body lumen, a recording medium on which a route selection assistance program is recorded, a route selection assistance method, and a diagnosis method.

A selection assistance system is disclosed for assisting in selecting a route of a living body lumen for delivering a medical instrument to a site within a living body via the living body lumen, the route selection assistance system including: a receiving section configured to receive an input of site information specifying a target site within the living body as a target of delivering the medical instrument; an image obtaining section configured to obtain image information on an inside of the living body of a target patient as the target of delivering the medical instrument; a route extracting section configured to extract a plurality of routes of the living body lumen, the plurality of routes allowing the medical instrument to be delivered to the target site on a basis of the image information obtained by the image obtaining section; a ranking assigning section including a route score calculating section configured to calculate route scores determined according to ease of delivery of the medical instrument at a time of delivery of the medical instrument via the routes and a patient score calculating section configured to calculate patient scores determined according to magnitude of a burden imposed on the target patient, the ranking assigning section assigning rankings to the plurality of routes extracted by the route extracting section by using the route scores and the patient scores; and an output section configured to output the plurality of routes extracted by the route extracting section and the rankings assigned by the ranking assigning section.

A computer readable recording medium on which a route selection assistance program according to the present disclosure is recorded is a computer readable recording medium on which a route selection assistance program assisting in selecting a route of a living body lumen for delivering a medical instrument to a site within a living body via the living body lumen is recorded, the route selection assistance program making a computer perform: receiving an input of site information specifying a target site within the living body as a target of delivering the medical instrument; obtaining image information on an inside of the living body of a target patient as a target of delivering the medical instrument; extracting a plurality of routes of the living body lumen, the plurality of routes allowing the medical instrument to be delivered to the target site, on a basis of the obtained image information; calculating route scores determined according to ease of delivery of the medical instrument at a time of delivery of the medical instrument via the routes, calculating patient scores determined according to magnitude of a burden imposed on the target patient, and assigning rankings to the extracted plurality of routes using the calculated route scores and the calculated patient scores; and outputting the extracted plurality of routes and the assigned rankings.

A route selection assistance method according to the present disclosure is a method of assisting in selecting a route of a living body lumen for delivering a medical instrument to a site within a living body via the living body lumen, the method including: receiving an input of site information specifying a target site within the living body as a target of delivering the medical instrument; obtaining image information on an inside of the living body of a target patient as the target of delivering the medical instrument; extracting a plurality of routes of the living body lumen, the plurality of routes allowing the medical instrument to be delivered to the target site, on a basis of the obtained image information; assigning rankings to the extracted plurality of routes by using route scores determined according to ease of delivery of the medical instrument at a time of delivery of the medical instrument via the routes and patient scores determined according to magnitude of a burden imposed on the target patient; and outputting the extracted plurality of routes and the assigned rankings.

A diagnosis method according to the present disclosure is a method for diagnosing a route of a living body lumen for delivering a medical instrument to a site within a living body via the living body lumen, the method including: receiving an input of site information specifying a target site within the living body as a target of delivering the medical instrument; obtaining image information on an inside of the living body of a target patient as the target of delivering the medical instrument; extracting a plurality of routes of the living body lumen, the plurality of routes allowing the medical instrument to be delivered to the target site, on a basis of the obtained image information; assigning rankings to the extracted plurality of routes by using route scores determined according to ease of delivery of the medical instru-ment at a time of delivery of the medical instrument via the routes and patient scores determined according to magnitude of a burden imposed on the target patient; and diagnosing the route from the extracted plurality of routes and the assigned rankings.

According to the route selection assistance system, the recording medium on which the route selection assistance program is recorded, the route selection assistance method, and the diagnosis method in accordance with the present disclosure, the ranking assigning section assigns rankings to the plurality of routes extracted by the route extracting section by using route scores determined according to relative ease of delivery of the medical instrument at a time of delivery of the medical instrument and patient scores determined according to the magnitude of a burden imposed on the target patient. The output section then outputs the plurality of routes extracted by the route extracting section and the rankings assigned by the ranking assigning section. An operator, for example, a doctor can thereby select an appropriate route rather easily from among the plurality of routes of living body lumens through which the medical instrument can be delivered to the target site as a target of a procedure in consideration of the ease of delivery of the medical instrument at a time of delivery of the medical instrument and the magnitude of a burden imposed on the target patient. Hence, according to the route selection assistance system, the recording medium on which the route selection assistance program is recorded, the route selection assistance method, and the diagnosis method in accordance with the present disclosure, it is possible to rather easily select a route of a living body lumen for delivering the medical instrument to a site within the living body via the living body lumen.

BRIEF DESCRIPTION OF THE DRAWINGS

FIG. 4 is a diagram schematically depicting a data structure of an introduction site list.

FIG. 9 is a block diagram depicting a functional configuration of a route extracting section of the route selection assistance system according to the first embodiment.

FIG. 12 is a schematic diagram depicting a screen of a display of the route selection assistance system according to the second embodiment.

FIG. 13A is a diagram schematically depicting a data structure of a medical instrument list.

FIG. 13B is a diagram schematically depicting a data structure of a device list.

FIG. 13C is a diagram schematically depicting a data structure of a device information list.

DETAILED DESCRIPTION

Figure 1:
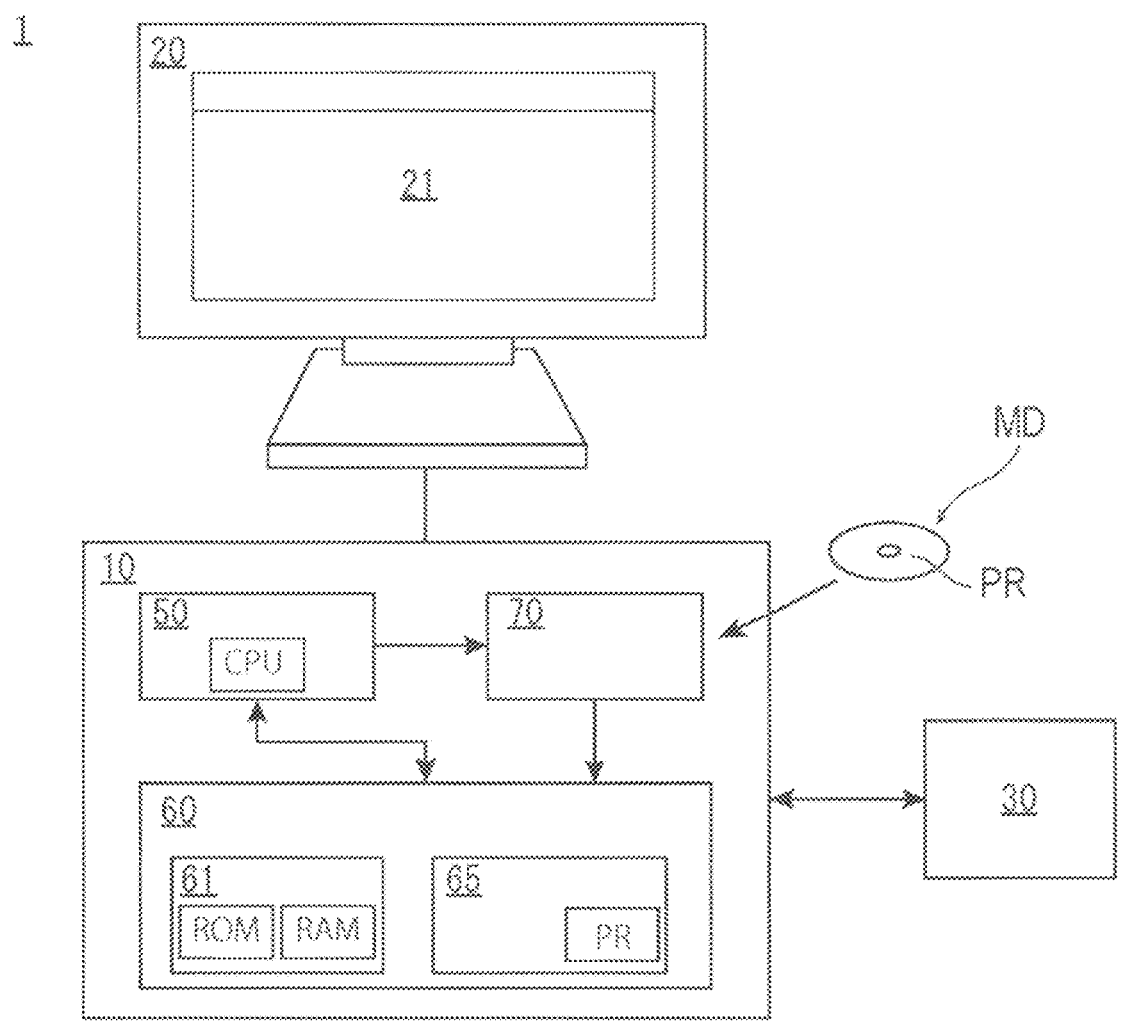
FIG. 1 is a schematic diagram depicting a device configuration of a route selection assistance system according to a first embodiment.

Embodiments of the present disclosure will hereinafter be described with reference to the drawings. It is to be noted that the dimensional ratios in the drawings are exaggerated for the convenience of description, and may be different from actual ratios.

First Embodiment

A route selection assistance system 1 according to the present embodiment is a route selection assistance system that assists in selecting a route RT of a blood vessel BV (corresponding to a living body lumen) for delivering a medical instrument to a site within a living body BD via the blood vessel BV.

Figure 2:
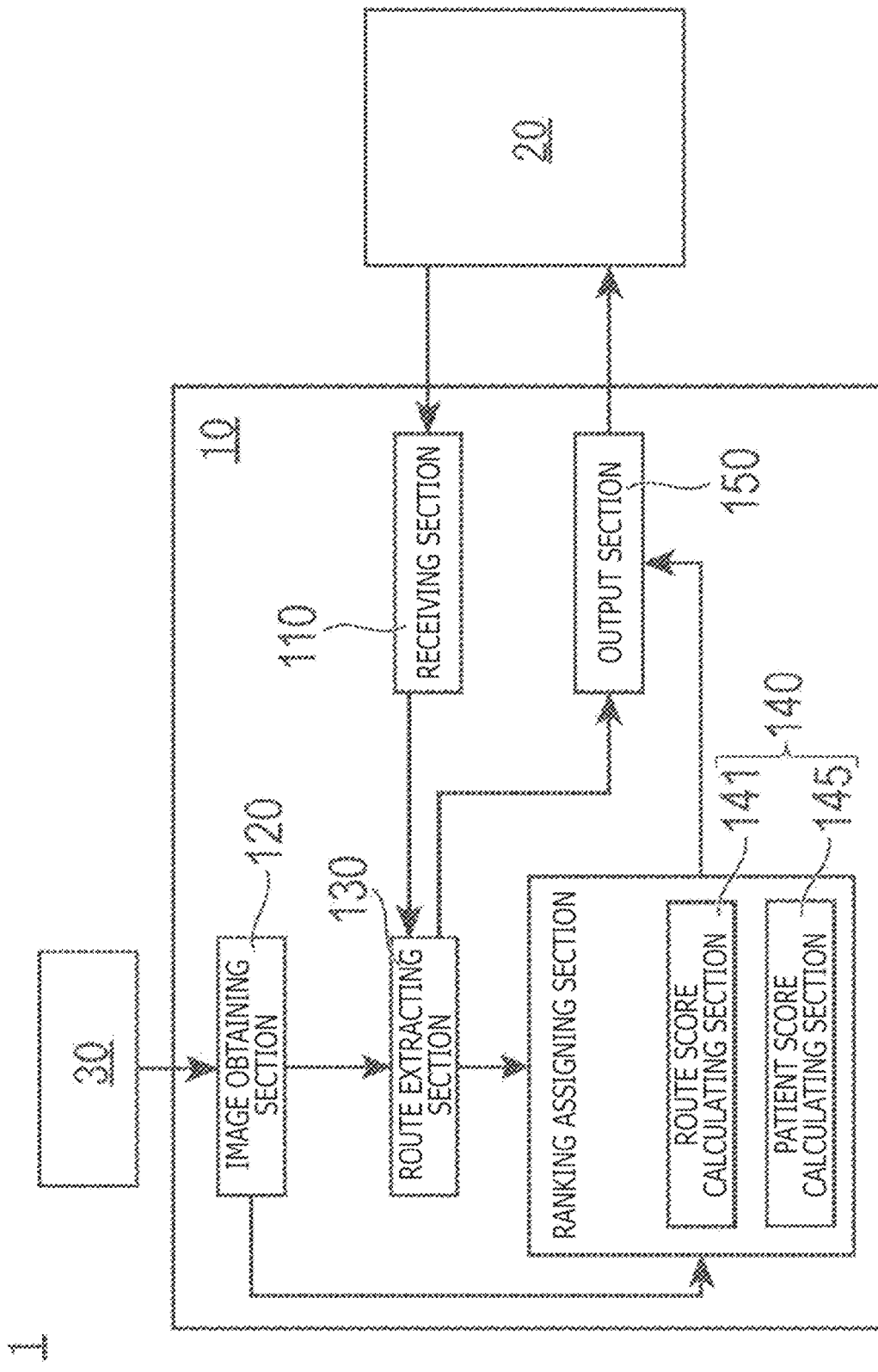
FIG. 2 is a block diagram depicting a functional configuration of the route selection assistance system according to the first embodiment.

FIG. 1 is a schematic diagram of assistance in explaining a device configuration of the route selection assistance system 1. FIG. 2 is a block diagram of assistance in explaining a functional configuration of the route selection assistance system 1. FIGS. 3 to 9 are diagrams of assistance in explaining various functions of the route selection assistance system 1.

A device configuration of the route selection assistance system 1 will be described.

Referring to FIG. 1, the route selection assistance system 1 includes a computer main unit 10 and a display 20. The computer main unit 10 is connected to an external server 30.

The computer main unit 10 includes an arithmetic unit 50, a storage device 60, and a reading device 70.

The arithmetic unit 50 performs operation on the basis of a program and data stored in the storage device 60. The arithmetic unit 50 can be any suitable central processing unit (CPU) (i.e., processor).

The storage device 60 includes a memory circuit 61 and a hard disk drive 65. The memory circuit 61 can include a read only memory (ROM) and a random access memory (RAM).

In accordance with an exemplary embodiment, the storage device 60 stores a basic program such as an operating system (OS), a route selection assistance program PR making the arithmetic unit 50 perform functions of the route selection assistance system 1, and data processed by the route selection assistance program PR.

The reading device 70 reads information recorded on a computer readable recording medium MD. The computer readable recording medium MD can be, for example, an optical disk such as a compact disk (CD)-ROM, or a digital video disk (DVD)-ROM, a universal serial bus (USB) memory, or a secure digital (SD) memory card. The reading device 70 can be, for example, a CD-ROM drive, or a DVD-ROM drive.

In accordance with an exemplary embodiment, the route selection assistance program PR is provided in a state of being recorded on the computer readable recording medium MD. The reading device 70 reads the route selection assistance program PR recorded on the computer readable recording medium MD. The route selection assistance program PR read by the reading device 70 is stored on the hard disk drive 65.

The display 20 is connected to the computer main unit 10. The display 20 transmits and receives information to and from the computer main unit 10.

The display 20 can include a screen 21 that inputs and outputs information. The display 20 outputs information received from the computer main unit 10 on the screen 21. The display 20 transmits information input via the screen 21 to the computer main unit 10. The display 20 can be any suitable touch panel display.

The computer main unit 10 transmits and receives information to and from the external server 30.

The computer main unit 10 and the external server 30 are connected to each other via a network. The kind (i.e., type) of the network is not particularly limited. For example, the network may be a network of a wired system using a local area network (LAN) cable or the like, or may be a network of a radio system using wireless fidelity (Wi-Fi) or the like.

A functional configuration of the route selection assistance system 1 will next be described.

Referring to FIG. 2, the route selection assistance system 1 includes a receiving section 110, an image obtaining section 120, a route extracting section 130, a ranking assigning section 140, and an output section 150.

Operation related to processing of the receiving section 110, the image obtaining section 120, the route extracting section 130, the ranking assigning section 140, and the output section 150 is performed by the arithmetic unit 50. Data processed by the receiving section 110, the image obtaining section 120, the route extracting section 130, the ranking assigning section 140, and the output section 150 is stored in the storage device 60.

Figure 3:
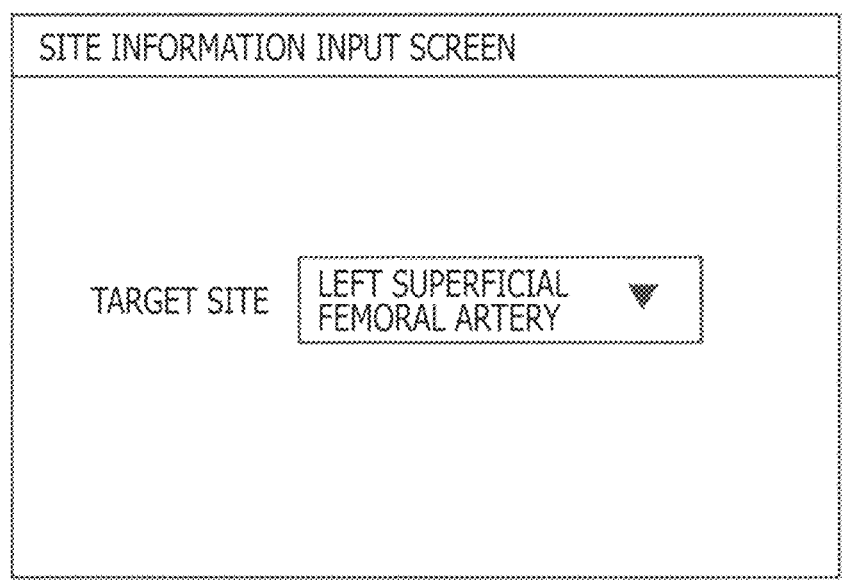
FIG. 3 is a schematic diagram depicting a screen of a display of the route selection assistance system according to the first embodiment.

Referring to FIG. 3, the receiving section 110 receives an input of site information specifying a target site RG as a target of a procedure to be performed by delivering a medical instrument. The receiving section 110 receives the input of the site information via the display 20.

The receiving section 110 displays one or a plurality of sites to be received as the target site RG as alternatives on the display 20, and receives a selection of a displayed site.

Though not particularly limited, the target site RG can be, for example, a left and a right common iliac artery, external iliac arteries, internal iliac arteries, common femoral arteries, superficial femoral arteries, deep femoral arteries, popliteal arteries, anterior tibial arteries, posterior tibial arteries, peroneal arteries, dorsalis pedis arteries, plantar arteries, and other arteries of lower limbs, or collateral circulations, peripheral blood vessels connected to arteries as described above.

The image obtaining section 120 obtains image information DT1 within the living body BD of a target patient as a target of a procedure to be performed by delivering a medical instrument.

Figure 6A:
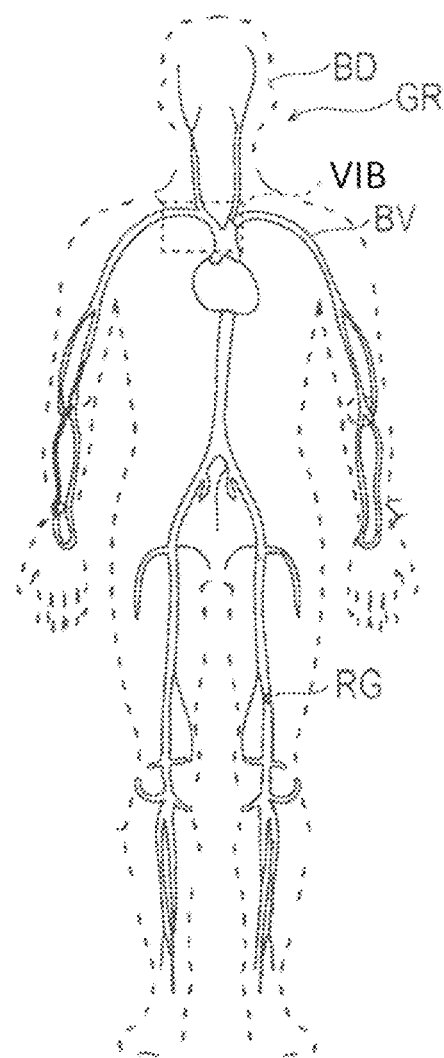
FIG. 6A is a diagram schematically depicting an image of a living body of a target patient.
Figures 8A, 8B:
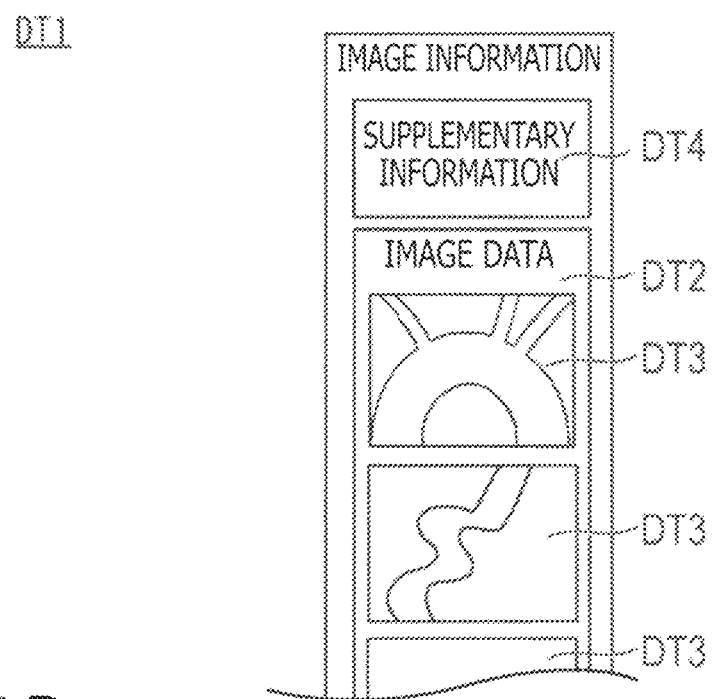
FIG. 8A is a diagram schematically depicting a data structure of image information.
FIG. 8B is a diagram schematically depicting a data structure of supplementary information.

Referring to FIG. 6A and FIG. 8A, the image information DT1 includes image data DT2 within the living body BD of the target patient which living body is photographed by a medical image photographing device. In accordance with an exemplary embodiment, the image data DT2 of the living body BD is three-dimensional image data.

Though not particularly limited, the medical image photographing device can be, for example, an X-ray computed tomography (CT) device or a magnetic resonance imaging (MRI) device.

Though not particularly limited, the data format of the image information DT1 can be, for example, digital imaging and communication in medicine (DICOM).

In accordance with an exemplary embodiment, the image information DT1 can be stored in the external server 30. The image obtaining section 120 obtains the image information DT1 from the external server 30 via the network.

In accordance with an exemplary embodiment, the route extracting section 130 extracts a plurality of routes RT of blood vessels BV through which a medical instrument can be delivered to the target site RG on the basis of the image information DT1 obtained by the image obtaining section 120. Though not particularly limited, the number of routes RT of blood vessels BV extracted by the route extracting section 130 can be, for example, 12 routes, preferably 8 routes, more preferably 6 routes.

For each candidate for a site as an access point at a time of introduction of a medical instrument from the outside of the living body BD to a blood vessel BV (which site will hereinafter be an introduction site RS), the route extracting section 130 extracts the route RT of the blood vessel BV leading from the target site RG to the introduction site RS.

Though not particularly limited, candidates for the introduction site RS can be, for example, a right radial artery, a right brachial artery, a right subclavian artery, a right carotid artery, a right femoral artery, a left radial artery, a left brachial artery, a left subclavian artery, a left carotid artery, and a left femoral artery. Candidates for the introduction site RS may also be, for example, a popliteal artery, an anterior tibial artery, a posterior tibial artery, a peroneal artery, a dorsalis pedis artery, a plantar artery, and other blood vessels of an ankle.

In addition, the radial artery may be a distal radial artery or a radial artery located in a snuff box.

Referring to FIG. 4, the route extracting section 130 extracts the route RT of the blood vessel BV leading from the target site RG to the introduction site RS by using an introduction site list LS1 in which candidates for the introduction site RS are recorded. The introduction site list LS1 can be, for example, stored in the external server 30. The route extracting section 130 obtains the introduction site list LS1 from the external server 30 via the network. Details of processing in the route extracting section 130 will be described later.

Referring to FIG. 2, the ranking assigning section 140 includes a route score calculating section 141 that calculates a route score SR determined according to ease of delivery of a medical instrument and a patient score calculating section 145 that calculates a patient score SP determined according to the magnitude (i.e., weight) of a relative burden imposed on the target patient.

The ranking assigning section 140 assigns rankings to the plurality of routes RT extracted by the route extracting section 130 by using the route score SR calculated by the route score calculating section 141 and the patient score SP calculated by the patient score calculating section 145.

The ranking assigning section 140 assigns rankings to the plurality of routes RT extracted by the route extracting section 130 in increasing order of a product SR×SP of the route score SR calculated by the route score calculating section 141 and the patient score SP calculated by the patient score calculating section 145.

The route score calculating section 141 calculates the route score SR on the basis of a length L of the route RT and a bending degree P of the route RT. The route score calculating section 141 calculates, as the route score SR, a product L×P of the length L of the route RT and the bending degree P of the route RT.

Figure 5:
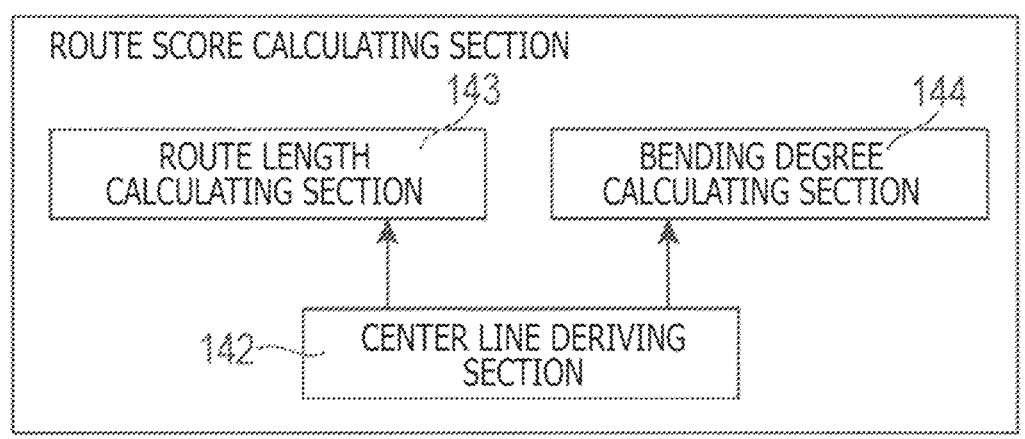
FIG. 5 is a block diagram depicting a functional configuration of a route score calculating section of the route selection assistance system according to the first embodiment.

Referring to FIG. 5, the route score calculating section 141 includes a center line deriving section 142 that calculates a center line CL of the route RT extracted by the route extracting section 130, a route length calculating section 143 that calculates the length L of the route RT, and a bending degree calculating section 144 that calculates the bending degree P of the route RT.

Figure 6B:
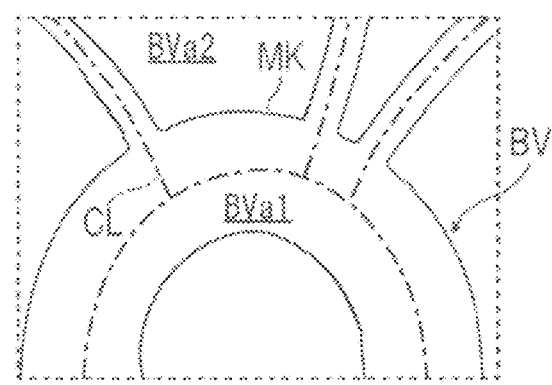
FIG. 6B is an enlarged view of a region enclosed by a broken line part VIB in FIG. 6A.

Referring to FIG. 6B, the image data DT2 includes a boundary marker MK indicating a boundary between an inside region BVa1 of the blood vessel BV and an outside region BVa2 of the blood vessel BV. The center line deriving section 142 calculates a center of the blood vessel BV on the basis of the boundary marker MK included in the image data DT2, and derives the center line CL of the blood vessel BV by connecting centers of the blood vessel BV leading from the target site RG to the introduction site RS to each other. In accordance with an exemplary embodiment, "a center of the blood vessel BV" refers to a center of a region enclosed by a blood vessel wall in a cross section of the blood vessel BV.

The route length calculating section 143 calculates the length of the center line CL calculated by the center line deriving section 142 as the length L of the route RT.

In accordance with an exemplary embodiment, the bending degree calculating section 144 calculates the bending degree of the center line CL derived by the center line deriving section 142 as the bending degree P of the route RT. In accordance with an exemplary embodiment, the "bending degree" is a sum total of the magnitude of bendings or curves calculated for respective parts bent or curved in the center line CL of the blood vessel BV. In accordance with an exemplary embodiment, "the magnitude of bendings" can be, for example, a curvature or the like.

The patient score calculating section 145 calculates the patient score SP by using an invasion degree (i.e., invasion level) of the route RT extracted by the route extracting section 130.

The invasion degree can be, for example, determined according to an amount of bleeding, for example, at a time of introduction of a medical instrument into the blood vessel BV via the introduction site RS, a time from an end of the procedure to the stopping of the bleeding, or the like. The invasion degree of the route RT whose introduction site RS can be a radial artery, for example, is smaller than the invasion degree of the route RT whose introduction site RS is, for example, a femoral artery.

Referring to FIG. 4, recorded in the introduction site list LS1 for each candidate for the introduction site RS is the invasion degree at a time of introduction of a medical instrument into the blood vessel BV via the corresponding introduction site RS.

The patient score calculating section 145 calculates the invasion degree of the route RT extracted by the route extracting section 130 by using the invasion degree recorded in the introduction site list LS1. The patient score calculating section 145 obtains the introduction site list LS1 from the external server 30 via the network.

Figure 7A:
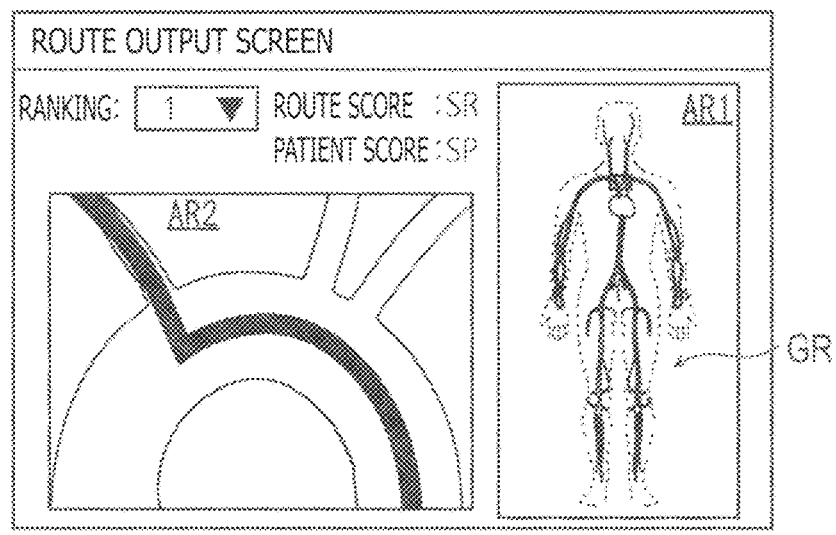
FIG. 7A is a schematic diagram depicting the screen of the display of the route selection assistance system according to the first embodiment.
Figure 7B:
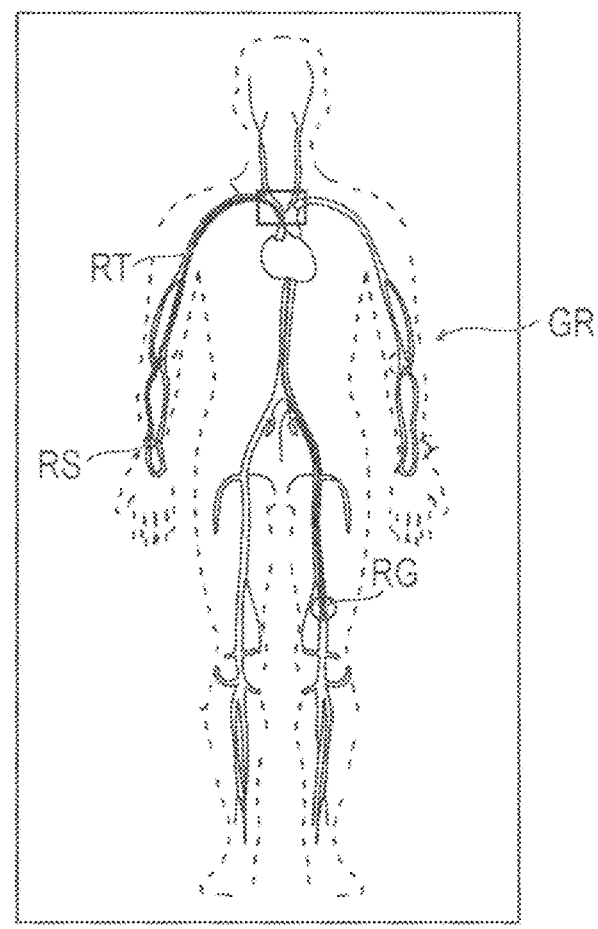
FIG. 7B is a schematic diagram depicting a route display region of the screen.

Referring to FIG. 7A and FIG. 7B, the output section 150 outputs, to the display 20, the plurality of routes RT extracted by the route extracting section 130, the rankings assigned by the ranking assigning section 140, the route score SR, and the patient score SP. The output section 150 outputs the plurality of routes RT extracted by the route extracting section 130 on the display 20 together with an image GR of the living body BD of the target patient.

In accordance with an exemplary embodiment, the output section 150 displays the plurality of routes RT extracted by the route extracting section 130 in a route display region AR1 of the display 20. The output section 150 displays an enlarged image of the plurality of routes RT extracted by the route extracting section 130 in a detailed display region AR2.

The receiving section 110 receives a selection of a route RT output to the display 20 by the output section 150. In response to the selection of the route RT which selection is received by the receiving section 110, the output section 150 displays, on the display 20, one route RT of the plurality of routes RT extracted by the route extracting section 130, a ranking corresponding to the one route RT, a route score SR, and a patient score SP.

Processing in the route extracting section 130 will next be explained in detail.

Referring to FIG. 8A and FIG. 8B, the image information DT1 includes divided image data DT3 obtained by dividing the image data DT2 into a plurality of pieces and supplementary information DT4 recorded as information about the divided image data DT3.

In accordance with an exemplary embodiment, the divided image data DT3 is data generated by dividing the image data DT2 according to sites of the blood vessel BV. For example, the divided image data DT3 is data generated by dividing the image data DT2, for example, for each site of a right subclavian artery, a brachiocephalic artery, an aortic arch, a thoracic aorta, an abdominal aorta, a left common iliac artery, a left external iliac artery, a left femoral artery, or the like. Divided images are identified by unique identifiers (hereinafter IDs).

Recorded as the supplementary information DT4 for each piece of divided image data DT3 are site information specifying a site of the blood vessel BV included in the corresponding divided image data DT3 and link information bidirectionally linking adjacent pieces of divided image data DT3 to each other.

Referring to FIG. 9, the route extracting section 130 can include: a target site image specifying section 131 that specifies the ID of a piece of divided image data DT3 including the target site RG from among the plurality of pieces of divided image data DT3 included in the image information DT1; an introduction site image specifying section 132 that specifies the ID of a piece of divided image data DT3 including a candidate for the introduction site RS from among the plurality of pieces of divided image data DT3 included in the image information DT1; and a route searching section 133 that searches for the route RT of the blood vessel BV leading from the target site RG to the introduction site RS.

The target site image specifying section 131 specifies the ID of the piece of divided image data DT3 including the target site RG by using the site information received by the receiving section 110 and the site information included in the supplementary information DT4.

The introduction site image specifying section 132 specifies the ID of a piece of divided image data DT3 including, for example, a candidate for the introduction site RS by using the introduction site list LS1 and the site information included in the supplementary information DT4.

The route searching section 133 searches for the route RT of the blood vessel BV leading from the target site RG to the introduction site RS by using the ID of a divided image specified by the target site image specifying section 131, the ID of a divided image specified by the introduction site image specifying section 132, and the link information included in the supplementary information DT4.

Description will next be made of a method of assisting in selecting the route RT of the blood vessel BV (corresponding to a living body lumen) for delivering a medical instrument to a site within a living body via the living body lumen (which method will hereinafter be a route selection assistance method).

Figure 10:
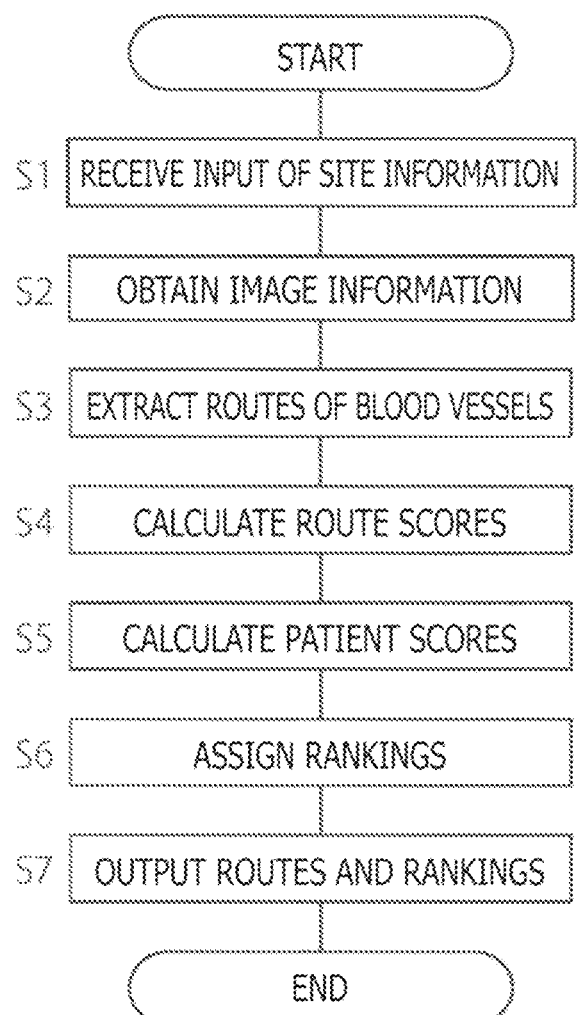
FIG. 10 is a flowchart of assistance in explaining a route selection assistance method according to the first embodiment.

Referring to FIG. 10, the route selection assistance method can includes: step S1 of receiving an input of site information; step S2 of obtaining the image information DT1; step S3 of extracting the routes RT of blood vessels BV; step S4 of calculating route scores SR; step S5 of calculating patient scores SP; step S6 of assigning rankings to the extracted routes RT; and step S7 of outputting the extracted routes RT and the rankings.

Step S1 of receiving an input of site information receives the input of the site information specifying the target site RG as a target of a procedure performed by delivering a medical instrument. In accordance with an exemplary embodiment, step S1 of receiving the input of the site information is performed by the receiving section 110.

Step S2 of obtaining the image information DT1 obtains the image information DT1 of the living body BD of the target patient as a target of a procedure performed by delivering a medical instrument. In accordance with an exemplary embodiment, step S2 of obtaining the image information DT1 is performed by the image obtaining section 120.

Step S3 of extracting the routes RT of blood vessels BV extracts a plurality of routes RT of living body lumens through which a medical instrument can be delivered to the target site RG on the basis of the obtained image information DT1. In accordance with an exemplary embodiment, step S3 of extracting the routes RT of the blood vessels BV is performed by the route extracting section 130.

Step S4 of calculating route scores SR calculates the route scores SR determined according to ease of delivery of a medical instrument at a time of delivery of the medical instrument via the routes RT. In accordance with an exemplary embodiment, step S4 of calculating the route scores SR is performed by the route score calculating section 141.

Step S5 of calculating patient scores SP calculates the patient scores SP determined according to the magnitude of a relative burden imposed on the target patient. In accordance with an exemplary embodiment, step S5 of calculating the patient scores SP is performed by the patient score calculating section 145.

Step S6 of assigning rankings assigns rankings to the plurality of extracted routes RT on the basis of the calculated route scores SR and the calculated patient scores SP. In accordance with an exemplary embodiment, step S6 of assigning the rankings is performed by the ranking assigning section 140.

Outputting step S7 outputs, to the display 20, the plurality of routes RT extracted in step S3 of extracting the routes RT of the blood vessels BV, the rankings assigned in step S6 of assigning the rankings, the route scores SR calculated in step S4 of calculating the route scores SR, and the patient scores SP calculated in step S5 of calculating the patient scores SP.

Outputting step S7 outputs, to the display 20, the routes RT, the rankings, the route scores SR, and the patient scores SP in order to assist an operator such as a doctor in selecting the route RT of a blood vessel BV for delivering a medical instrument to the target site RG within the living body BD via the blood vessel BV.

Outputting step S7 outputs the plurality of routes RT extracted by the route extracting section 130 to the display 20 together with the image GR of the living body BD of the target patient.

Outputting step S7 is performed by the output section 150.

Description will next be made of a method of diagnosing the route RT of a blood vessel BV for delivering a medical instrument to a site within the living body BD via the blood vessel BV (corresponding to a living body lumen) (which method will hereinafter be a diagnosis method).

The diagnosis method according to the present embodiment includes a step of diagnosing a route RT from the plurality of routes RT extracted in step S3 of extracting the routes RT of the blood vessels BV and the rankings assigned in step S6 of assigning the rankings in addition to steps S1 to S6 of the route selection assistance method described above.

The step of diagnosing a route RT diagnoses a route RT assigned a high ranking in step S6 of assigning the rankings as a more appropriate route RT as compared with a route RT having a low ranking from a viewpoint of the ease of delivering a medical instrument at a time of delivery of the medical instrument via the route RT and the magnitude of a burden imposed on the target patient.

Description will next be made of an example of usage of the route assistance system according to the present embodiment. In the following, description will be made by taking as an example a case where six sites of a right radial artery, a right brachial artery, a right femoral artery, a left radial artery, a left brachial artery, and a left femoral artery are recorded in the introduction site list LS1 (see FIG. 4). In the following, description will be made by taking as an example a case where a left superficial femoral artery (SFA) is to be treated.

Referring to FIG. 3, by operating the display 20, an operator inputs a "left superficial femoral artery" as site information specifying the target site RG as a target of a procedure performed by delivering a medical instrument.

The image obtaining section 120 obtains the image information DT1 on the inside of the living body BD of the target patient as a target of a procedure performed by delivering a medical instrument from the external server 30 (see FIG. 1) via the network.

In accordance with an exemplary embodiment, the route extracting section 130 extracts six routes RT of blood vessels BV corresponding to six candidates for the introduction site RS, the six candidates being a right radial artery, a right brachial artery, a right femoral artery, a left radial artery, a left brachial artery, and a left femoral artery recorded in the introduction site list LS1 (see FIG. 4).

For each of the six routes RT extracted by the route extracting section 130, the route score calculating section 141 calculates a route score SR on the basis of the length L of the route RT and the bending degree P of the route RT. For each of the six routes RT extracted by the route extracting section 130, the patient score calculating section 145 calculates a patient score SP by using an invasion degree.

In the present usage example, the route score SR is decreased in order of the route RT whose introduction site RS is a right radial artery (left radial artery), the route RT whose introduction site RS is a right brachial artery (left brachial artery), and the route RT whose introduction site RS is a right femoral artery (left femoral artery). In contrast to this, the patient score SP is decreased in order of the route RT whose introduction site RS is the right femoral artery (left femoral artery), the route RT whose introduction site RS is the right brachial artery (left brachial artery), and the route RT whose introduction site RS is the right radial artery (left radial artery).

In the present usage example, the product SR×SP of the route score SR and the patient score SP is decreased in order of the route RT whose introduction site RS is the right femoral artery (left femoral artery), the route RT whose introduction site RS is the right brachial artery (left radial artery), and the route RT whose introduction site RS is the right radial artery (left radial artery).

In accordance with an exemplary embodiment, the ranking assigning section 140 assigns rankings to the plurality of routes RT extracted by the route extracting section 130 in increasing order of the product SR×SP of the route score SR calculated by the route score calculating section 141 and the patient score SP calculated by the patient score calculating section 145.

The output section 150 outputs, to the display 20, the plurality of routes RT extracted by the route extracting section 130, the rankings assigned by the ranking assigning section 140, and the route scores SR and the patient scores SP (see FIG. 7A and FIG. 7B).

In accordance with an exemplary embodiment, the operator such as a doctor refers to the routes RT of the blood vessels BV, the rankings, and the route scores SR and the patient scores SP output to the display 20, and thereby selects an appropriate route RT with consideration given to the relative ease of delivery of a medical instrument at a time of delivery of the medical instrument and the magnitude of a relative burden imposed on the target patient.

According to the route selection assistance system 1, the recording medium MD on which the route selection assistance program PR is recorded, the route selection assistance method, and the diagnosis method in accordance with the present embodiment, the ranking assigning section 140 assigns rankings to the plurality of routes RT extracted by the route extracting section 130 by using the route scores SR determined according to the ease of delivery of a medical instrument at a time of delivery of the medical instrument and the patient scores SP determined according to the magnitude of a burden imposed on the target patient. The output section 150 then outputs the plurality of routes RT extracted by the route extracting section 130 and the rankings assigned by the ranking assigning section 140. The operator such as a doctor can thereby select an appropriate route RT rather easily from among the plurality of routes RT of blood vessels BV through which a medical instrument can be delivered to the target site RG as a target of a procedure in consideration of the ease of delivery of the medical instrument at a time of the delivery of the medical instrument and the magnitude of a relative burden imposed on the target patient. Hence, according to the route selection assistance system 1, the recording medium MD on which the route selection assistance program PR is recorded, and the route selection assistance method in accordance with the present disclosure, it is possible to rather easily select the route RT of a blood vessel BV for delivering a medical instrument to a site within the living body BD via the blood vessel BV. Such an effect is particularly remarkable in a case where the number of sites of the blood vessel BV which sites are to be passed is increased, for example, in a case where the blood vessel BV of a lower limb is treated by using TRI or the like.

In addition, according to the route selection assistance system 1, the recording medium MD on which the route selection assistance program PR is recorded, the route selection assistance method, and the diagnosis method in accordance with the present embodiment, the route score calculating section 141 calculates a route score SR by using the length of a route RT and the bending degree P of the route RT. The ranking assigning section 140 can thereby evaluate the relative ease of delivery of a medical instrument at a time of delivery of the medical instrument more appropriately, and rank the routes RT. Therefore, the operator can rather easily select a more appropriate route RT from among the plurality of routes RT of the blood vessels BV through which a medical instrument can be delivered to the target site RG in consideration of the relative ease of delivery of the medical instrument at a time of delivery of the medical instrument. Such an effect is particularly remarkable, for example, in a case where an appropriate route RT is selected from among the plurality of routes RT including sites greatly differing in the relative magnitude of bending or curvature for each target patient, the sites being a right radial artery, a right brachial artery, a right axillary artery, a right subclavian artery, a right brachiocephalic artery, a left radial artery, a left brachial artery, a left axillary artery, a right subclavian artery, a brachiocephalic artery, an aortic arch, a thoracic aorta, an abdominal aorta (descending aorta), an aortailiac bifurcation, left or right one or both of common iliac arteries, external iliac arteries, internal iliac arteries, common femoral arteries, superficial femoral arteries, and deep femoral arteries, and further, as required, popliteal arteries, anterior tibial arteries, posterior tibial arteries, peroneal arteries, dorsalis pedis arteries, plantar arteries, collateral circulations, or the like.

In addition, according to the route selection assistance system 1, the recording medium MD on which the route selection assistance program PR is recorded, the route selection assistance method, and the diagnosis method in accordance with the present embodiment, the patient score calculating section 145 calculates a patient score SP by using the invasion degree of a route RT. The ranking assigning section 140 can thereby evaluate the magnitude of a relative burden imposed on the target patient more appropriately, and rank the routes RT. Therefore, the operator can rather easily select a more appropriate route RT from among the plurality of routes RT of the blood vessels BV through which a medical instrument can be delivered to the target site RG in consideration of the magnitude of a burden imposed on the target patient.

Second Embodiment

Figure 11:
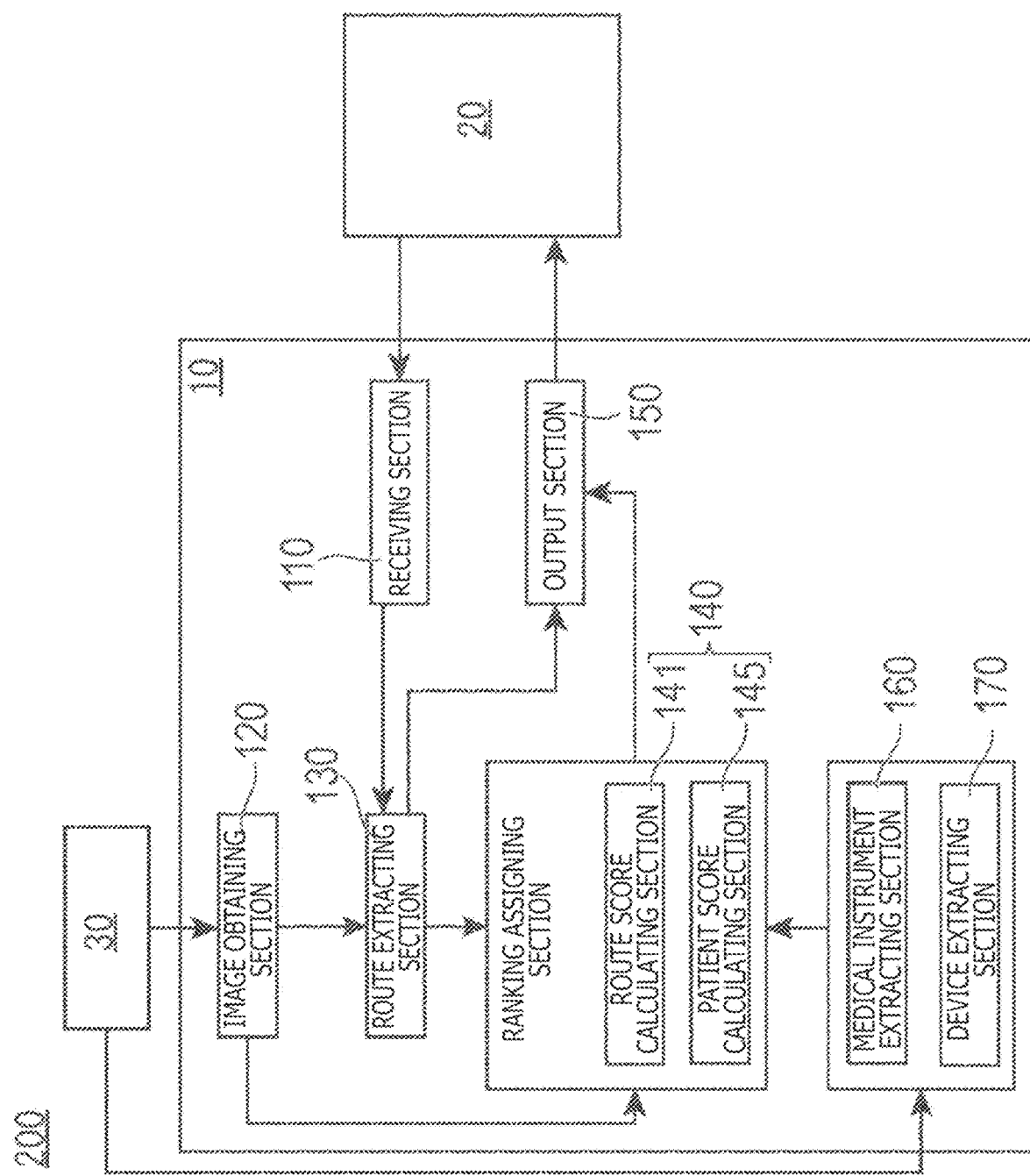
FIG. 11 is a block diagram depicting a functional configuration of a route selection assistance system according to a second embodiment.

Referring to FIG. 11, a route selection assistance system 200 according to a present embodiment includes a medical instrument extracting section 160 that extracts a kind (i.e., type) of medical instrument to be used for a procedure and a device extracting section 170 that extracts useable device candidates according to the kind of medical instrument extracted by the medical instrument extracting section 160, in addition to the functional configuration of the route selection assistance system 1 according to the foregoing embodiment.

The route selection assistance system 200 according to the present embodiment will be described in the following. In accordance with an exemplary embodiment, a device configuration of the route selection assistance system 200 according to the present embodiment is the same as the device configuration of the route selection assistance system 1 according to the foregoing embodiment. A functional configuration of the route selection assistance system 200 according to the present embodiment is the same as the functional configuration of the route selection assistance system 1 according to the foregoing embodiment except that the functional configuration of the route selection assistance system 200 according to the present embodiment further includes the medical instrument extracting section 160 and the device extracting section 170. The same devices and functional blocks as in the route selection assistance system 1 according to the foregoing embodiment are identified by the same reference numerals, and description same devices and functional blocks as in the route selection assistance system 1 will be omitted.

Referring to FIG. 12, the receiving section 110 receives an input of procedure information specifying a kind (i.e., type) of procedure to be performed by delivering a medical instrument to the target site RG via a blood vessel BV (corresponding to a living body lumen). The kinds of procedure can be, for example, expansion or piercing of a constriction in the blood vessel BV, excavation of the constriction of the blood vessel BV, imaging of the inside region BVa1 of the blood vessel BV, or releasing of a drug within the blood vessel BV. Except for receiving an input of procedure information, functions of the receiving section 110 are the same as the functions of the receiving section 110 in the route assistance system according to the foregoing embodiment.

In accordance with an exemplary embodiment, the medical instrument extracting section 160 extracts one or a plurality of kinds of medical instruments to be used for the kind of procedure specified by the procedure information. The kinds of medical instruments can be, for example, an introducer sheath, a guide wire, an imaging catheter, a micro-catheter, an angiographic catheter, a guide wire support catheter, a guiding catheter, a balloon catheter, a balloon-expandable stent, a self-expandable stent, a drug releasing stent, a drug releasing balloon, a directional coronary atherectomy (DCA) catheter, a microdissection catheter, a laser ablation catheter, and a catheter for image diagnosis.

The catheter for image diagnosis can be, for example, a catheter for obtaining an image by using an intravascular ultrasound diagnosis method (IVUS) or an optical coherence tomography diagnosis method (OCT).

In accordance with an exemplary embodiment, the device extracting section 170 extracts a useable device candidate for each kind of medical instrument extracted by the medical instrument extracting section 160. In accordance with an exemplary embodiment, the device extracting section 170 extracts the useable device candidate on the basis of the presence (i.e., availability) or absence (i.e., not available) of stock of a device.

In a case where there are a plurality of useable device candidates, the device extracting section 170 extracts the plurality of device candidates within a range not exceeding an upper limit number. Though not particularly limited, the upper limit number can be, for example, about 10 for each device.

In a case where there is no useable device, the number of device candidates extracted by the device extracting section 170 is zero.

Referring to FIGS. 13A to C, the external server 30 stores a medical instrument list LS2 recording kinds of medical instruments to be used for each kind of procedure, a device list LS3 recording device candidates for each kind of medical instrument, and a device information list LS4 recording the presence or absence of stock of a device for each device candidate.

The device list LS3 records commercially available devices for each kind of medical instrument. In accordance with an exemplary embodiment, the devices can be identified, for example, by unique device identifiers. The unique device identifiers can be, for example, the manufacturer name of a manufacturer selling devices, a model name, a pharmaceutical approval number, a product code, bar code data, a product name, and a lot number.

In accordance with an exemplary embodiment, the device information list LS4 records the presence or absence of stock of devices in a facility in which the route selection assistance system 200 is used.

The medical instrument extracting section 160 extracts kinds of medical instruments by using the medical instrument list LS2. In accordance with an exemplary embodiment, for example, the device extracting section 170 extracts useable device candidates by using the device list LS3 and the device information list LS4.

The ranking assigning section 140 adjusts rankings assigned to the plurality of routes RT extracted by the route extracting section 130 on the basis of a result of the device extraction by the device extracting section 170.

The ranking assigning section 140 decreases the ranking of a route RT for which no useable device is extracted in the device extracting section 170.

Figure 14:
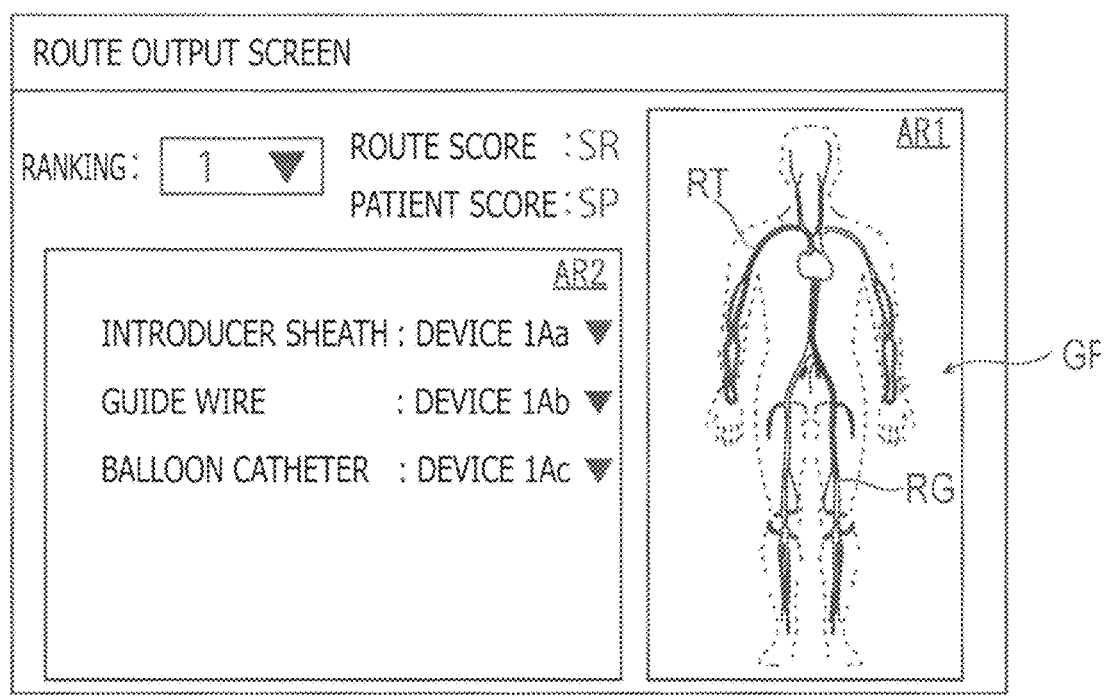
FIG. 14 is a schematic diagram depicting the screen of the display of the route selection assistance system according to the second embodiment.

Referring to FIG. 14, the output section 150 outputs the device candidates extracted by the device extracting section 170 to the display 20 in addition to information output by the output section 150 of the route selection assistance system 1 according to the foregoing embodiment.

The output section 150 outputs, to the display 20, the routes RT, the rankings, the route scores SR, and the patient scores SP in order to assist an operator such as a doctor in selecting a device to be used for a procedure performed by delivering a medical instrument to the target site RG within the living body BD via the blood vessel BV.

According to the route selection assistance system 200 in accordance with the present embodiment, the receiving section 110 receives an input of procedure information specifying a kind of procedure to be performed by delivering a medical instrument via the blood vessel BV. The route selection assistance system 200 according to the present embodiment includes the medical instrument extracting section 160 that extracts kinds of medical instruments to be used for the procedure specified by the procedure information and the device extracting section 170 that extracts useable device candidates for each kind of medical instrument extracted by the medical instrument extracting section 160. The output section 150 then outputs a result of the extraction of the device candidates by the device extracting section 170. Thus, the operator can rather easily select a device to be used for a procedure performed by delivering a medical instrument via the blood vessel BV. Therefore, a relative burden on the operator at a time of performing a procedure by delivering a medical instrument via the blood vessel BV can be reduced.

In addition, according to the route selection assistance system 200, the recording medium MD on which the route selection assistance program PR can be recorded, and the route selection assistance method in accordance with the present embodiment, the ranking assigning section 140 can adjust the rankings assigned to the plurality of routes RT extracted by the route extracting section 130 on the basis of a result of extraction of device candidates by the device extracting section 170. Thus, the operator can rather easily select a more appropriate route RT from among the plurality of routes RT of blood vessels BV through which a medical instrument can be delivered to the target site RG according to the useable device candidates.

First Modification

In the foregoing first and second embodiments, the patient score calculating section 145 calculates the magnitude of a relative burden imposed on the target patient by using an invasion degree. However, the patient score calculating section 145 may also calculate a patient score SP using patient information recording characteristics of the target patient.

The patient information can be stored in the external server 30. The patient score calculating section 145 obtains the patient information from the external server 30 via the network.

In accordance with an exemplary embodiment, the patient information can include information about the anamnesis (i.e., medical history) of the target patient. The information about the anamnesis or medical history of the target patient can include procedure history information recording history information about a procedure on the blood vessel BV. The procedure on the blood vessel BV can be, for example, placement of a stent or a graft. In accordance with an exemplary embodiment, the procedure history information can include information specifying a site of the blood vessel BV on which site the procedure is performed.

In accordance with an exemplary embodiment, the patient score calculating section 145 calculates a patient score SP using the information about the anamnesis or medical history of the target patient. Using the procedure history information, the patient score calculating section 145 calculates that a patient score SP for a route RT including the blood vessel BV on which the procedure is performed is relatively high as compared with a route RT not including the blood vessel BV on which the procedure is performed.

According to the route selection assistance system, the recording medium MD on which the route selection assistance program PR is recorded, and the route selection assistance method in accordance with the present modification, the patient score calculating section 145 calculates a patient score SP using information about the characteristics of the target patient. The ranking assigning section 140 can thereby evaluate the magnitude of a relative burden imposed on the target patient more appropriately, and rank the routes RT. Therefore, the operator can rather easily select an even more appropriate route RT from among the plurality of routes RT of the blood vessels BV through which a medical instrument can be delivered to the target site RG in consideration of the magnitude of a relative burden imposed on the target patient.

Second Modification

In the foregoing first and second embodiments, the receiving section 110 displays one or a plurality of sites to be received as the target site RG as alternatives on the display 20, and receives a selection of a displayed site.

Figure 15A:
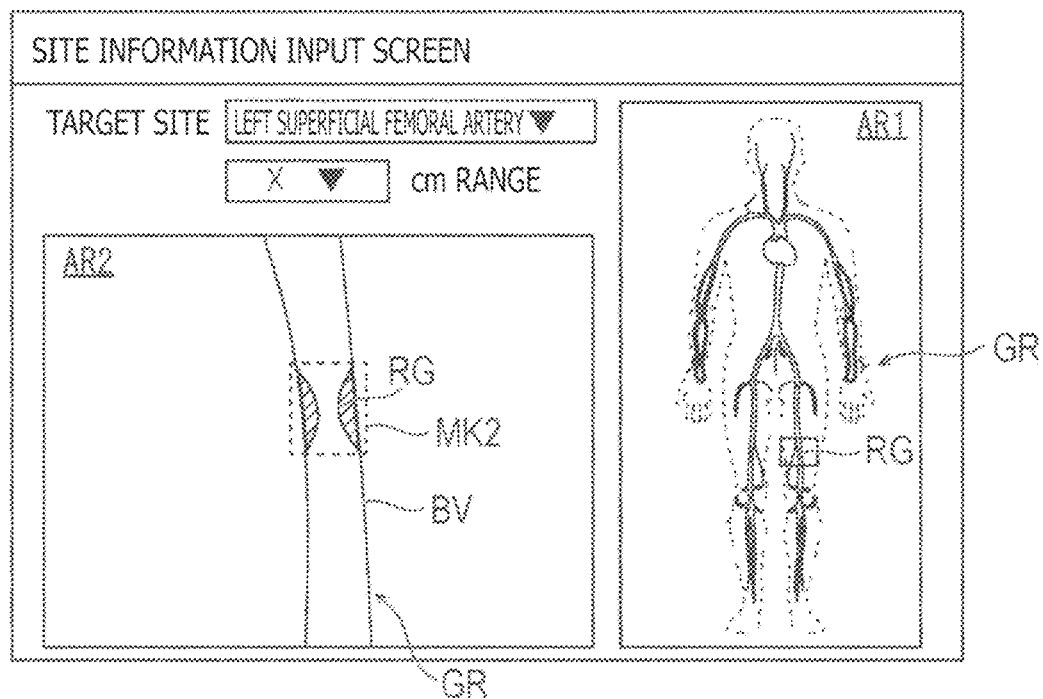
FIG. 15A is a schematic diagram depicting a screen of a display of a route selection assistance system according to one mode of a second modification.

Referring to FIG. 15A, for the site displayed on the display 20 as an alternative, the receiving section 110 may further receive a selection of a range of the site as a target of delivering a medical instrument. The operator, for example, a doctor can select the target site RG in a more detailed and accurate manner by selecting the range of the site as a target of delivering a medical instrument.

At this time, the receiving section 110 may display the image GR of the living body BD of the target patient on the display 20, and display the range selected as the site as a target of delivering a medical instrument in the image GR by a distinguishable marker MK2.

Figure 15B:
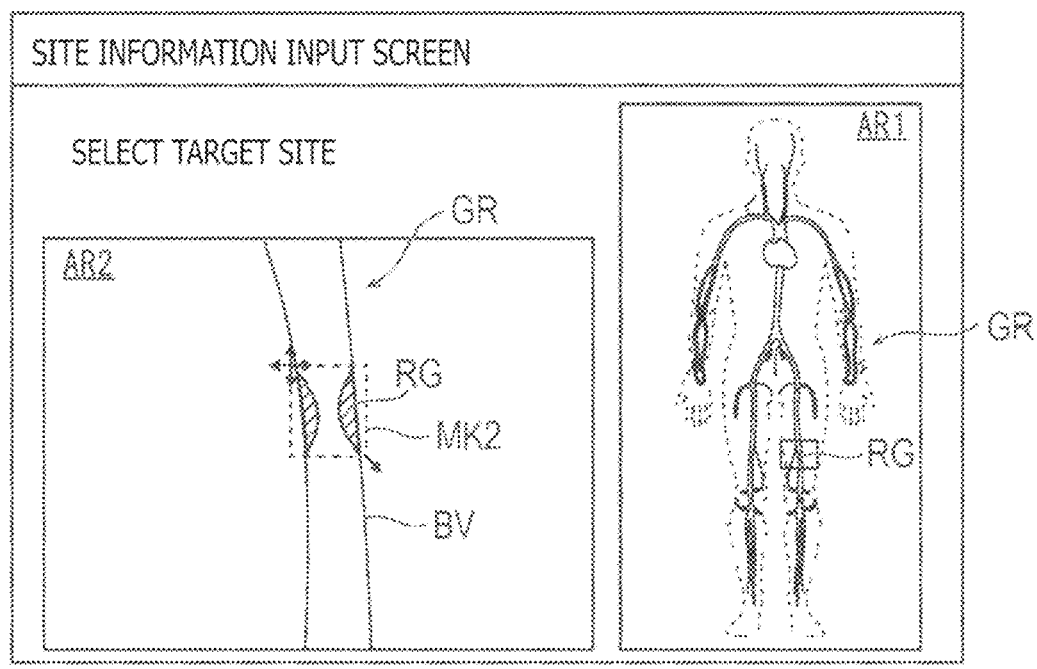
FIG. 15B is a schematic diagram depicting a screen of a display of a route selection assistance system according to another mode of the second modification.

In addition, referring to FIG. 15B, the receiving section 110 may display the image GR of the living body BD of the target patient on the display 20, and receive a selection of the target site RG in the image GR. In accordance with an exemplary embodiment, the operator, for example, a doctor can select the target site RG by tracing the target site RG by a finger or the like on the image GR displayed on the display 20. Therefore, according to the route selection assistance system in accordance with the present modification, the selection of the target site RG can be facilitated, and the selection of the target site RG can be made in a more detailed and accurate manner.

Third Modification

In the foregoing second embodiment, the device extracting section 170 extracts useable device candidates on the basis of the presence or absence of stock of devices (i.e., availability of the devices).

The device extracting section 170 may further narrow down the useable device candidates extracted on the basis of the presence or absence of stock of devices by using characteristics of the devices.

For example, the device extracting section 170 may exclude a device whose device length is less than the length L of the route RT from the useable device candidates extracted on the basis of the presence or absence of stock of devices.

The route selection assistance system, the recording medium on which the route selection assistance program is recorded, and the route selection assistance method have been described above through embodiments and modifications of the route selection assistance system, the recording medium on which the route selection assistance program is recorded, and the route selection assistance method. However, the present disclosure is not limited to only configurations described in the embodiments, but can be changed as appropriate on the basis of the description of claims.

For example, in the foregoing embodiments and the modifications of the foregoing embodiments, a blood vessel of a lower limb is illustrated as the target site. However, the target site is not particularly limited. For example, the target site may be a blood vessel in a brain, a heart, or the like. Further, in the foregoing embodiments and the modifications of the foregoing embodiments, description has been made by taking as an example a case where the living body lumen is a blood vessel. However, the living body lumen is not limited to a blood vessel, but may be a vessel, a bile duct, an oviduct, a hepatic duct, a trachea, an esophagus, or a urethra.

In addition, the patient score calculating section calculates a patient score using history information about a procedure on a blood vessel as information about the characteristics of the target patient. However, the patient score calculating section may calculate a patient score using information such as a tendency toward spasm (abnormal contraction of a blood vessel which contraction accompanies convulsion) because of a tendency toward tonus (i.e., constant low-level activity of a body tissue) or an onset history of constriction, occlusion, or the like as the information about the characteristics of the target patient. In this case, the patient score calculating section calculates that the patient score of a route including a blood vessel site where there is an onset history of spasm or the like is high as compared with the patient score of a route not including a blood vessel site where there is an onset history of spasm or the like. In addition, the patient score calculating section may calculate a patient score by combining the information about the characteristics of the target patient and an invasion degree with each other.

In the foregoing embodiments and the modifications of the foregoing embodiments, the output section outputs, to the display, the plurality of routes extracted by the route extracting section, the rankings assigned by the ranking assigning section, the route scores, and the patient scores. However, the output section may output the plurality of routes extracted by the route extracting section, the rankings assigned by the ranking assigning section, the route scores, and the patient scores as data to the external server. In this case, the route of a living body lumen can be expressed as a set of coordinates with the target site as an origin.

In addition, in the foregoing embodiments and the modifications of the foregoing embodiments, the output section displays one of the plurality of routes extracted by the route extracting section on the display in response to a selection of the route which selection is received by the receiving section. However, the output section may simultaneously display the plurality of routes extracted by the route extracting section on the display. In this case, the output section may display the plurality of routes extracted by the route extracting section on the display in different colors.

In addition, in the foregoing embodiments and the modifications of the foregoing embodiments, the image information includes image data and supplementary information. However, it suffices for the image information to include at least image data of the living body lumen of the target patient, and the supplementary information is not an essential requirement.

In addition, the image data does not have to include a boundary marker. Even in this case, the center line calculating section of the route score calculating section can derive the center line of the blood vessel on the basis of the image data by using a publicly known image processing technology or the like.

In addition, the image data does not need to be divided for each site of the living body lumen. Even when the image data is not divided for each site of the living body lumen, the route extracting section can extract the route of the living body lumen through which a medical instrument can be delivered to the target site by using a publicly known image processing technology or the like on the basis of the image data.

In addition, in the foregoing embodiments and the modifications of the foregoing embodiments, the route selection assistance program recorded on the computer readable recording medium is read by the reading device and stored in the storage device, and thereby the route selection assistance system functions. However, the route selection assistance system may be provided in a state in which the route selection assistance program is stored in the storage device in advance. In addition, a part or all of the functions of the route selection assistance system may be implemented by a programmable circuit structure such as a field programmable gate array (FPGA). In this case, a part or the whole of the route selection assistance program is described in a hardware description language such as Verilog.

In addition, in the foregoing embodiments and the modifications of the foregoing embodiments, the receiving section receives an input of site information or the like via the touch panel display. However, in the route selection assistance system, an input device is not limited to the touch panel display, but any suitable input device can be used. For example, the route selection assistance system may include a mouse or a pen tablet as the input device in addition to a display that is not the touch panel display. The operator, for example, a doctor can input site information by operating the mouse or the pen tablet.

In addition, in the foregoing embodiments and the modifications of the foregoing embodiments, the computer main unit and the display are configured as separate parts. However, the computer main unit and the display may be configured integrally with each other, or the display may be incorporated in the computer main unit.

In addition, in the foregoing embodiments and the modifications foregoing embodiments, the image obtaining section obtains image information from the external server. However, the image obtaining section may be configured by using an image photographing device for medical use, for example, an X-ray CT device, or an MRI device.

The detailed description above describes to a route selection assistance system assisting in selecting a route of a living body lumen for delivering a medical instrument to a site within a living body via the living body lumen, a recording medium on which a route selection assistance program is recorded, a route selection assistance method, and a diagnosis method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A route selection assistance system for assisting in selecting a route of a living body lumen for delivering a medical instrument to a site within a living body via the living body lumen via an introduction site, the route selection assistance system comprising:
   a receiving section configured to receive an input of site information specifying a target site within the living body as a target of delivering the medical instrument and a plurality of introduction sites and to receive an input of procedure information specifying a procedure to be performed by delivering the medical instrument to the target site via the living body lumen;
   an image obtaining section configured to obtain image information on an inside of the living body of a target patient as the target of delivering the medical instrument from the plurality of introduction sites;
   a route extracting section configured to extract a plurality of routes of the living body lumen, the plurality of routes allowing the medical instrument to be delivered to the target site from the plurality of introduction sites on a basis of the image information obtained by the image obtaining section;
   a ranking assigning section including a route score calculating section configured to calculate route scores determined according to ease of delivery of the medical instrument at a time of delivery of the medical instrument via the plurality of routes and a patient score calculating section configured to calculate patient scores determined according to magnitude of a burden imposed on the target patient, the ranking assigning section assigning rankings to the plurality of routes extracted by the route extracting section by using the route scores and the patient scores;
   a medical instrument extracting section configured to extract medical instruments used for the procedure specified by the procedure information;
   a device extracting section configured to extract useable device candidates for the medical instruments extracted by the medical instrument extracting section, the useable device candidates being available for the procedure specified by the procedure information and in a case where there are no useable device candidates, a number of the useable device candidates extracted by the device extracting section is zero, and wherein the ranking assigning section decreases a ranking of a route of the plurality of routes extracted for which the number of useable device candidates extracted by the device extracting section is zero; and
   an output section configured to output the plurality of routes extracted by the route extracting section and the rankings assigned by the ranking assigning section to the plurality of routes extracted by the route extracting section using the route scores and the patient scores and to output a result of the extraction of the useable device candidates by the device extracting section.

2. The route selection assistance system according to claim 1, wherein
   the ranking assigning section is configured to adjust the rankings assigned to the plurality of routes extracted by the route extracting section on a basis of the result of extraction of the useable device candidates by the device extracting section.

3. The route selection assistance system according to claim 1, wherein
   the route score calculating section is configured to calculate lengths of the plurality of routes extracted by the route extracting section and bending degrees of the plurality of routes on a basis of the image information on the inside of the living body of the target patient, and is configured to calculate the route scores using the calculated lengths of the plurality of routes and the calculated bending degrees of the plurality of routes.

4. The route selection assistance system according to claim 1, wherein
   the patient score calculating section is configured to calculate invasion degrees of the plurality of routes extracted by the route extracting section, and is configured to calculate the patient scores using the calculated invasion degrees of the plurality of routes.

5. The route selection assistance system according to claim 1, wherein
   the patient score calculating section obtains patient information related to a characteristic of the target patient, and calculates the patient scores on a basis of the patient information.

6. A non-transitory computer readable recording medium on which a route selection assistance program assisting in selecting a route of a living body lumen for delivering a medical instrument to a site within a living body via the living body lumen via an introduction site is recorded, the route selection assistance program making a computer perform:
- receiving an input of site information specifying a target site within the living body as a target of delivering the medical instrument and a plurality of introduction sites and an input of procedure information specifying a procedure to be performed by delivering the medical instrument to the target site via the living body lumen;
- obtaining image information on an inside of the living body of a target patient as a target of delivering the medical instrument from the plurality of introduction sites;
- extracting a plurality of routes of the living body lumen, the plurality of routes allowing the medical instrument to be delivered to the target site from the plurality of introduction sites, on a basis of the obtained image information;
- calculating route scores determined according to ease of delivery of the medical instrument at a time of delivery of the medical instrument via the plurality of routes;
- calculating patient scores determined according to magnitude of a burden imposed on the target patient;
- assigning rankings to the extracted plurality of routes using the calculated route scores and the calculated patient scores;
- extracting medical instruments used for the procedure specified by the procedure information;
- extracting useable device candidates for the medical instruments extracted for the procedure specified by the procedure information, the useable device candidates being available for the procedure specified by the procedure information and in a case where there are no useable device candidates, a number of the useable device candidates extracted is zero;
- decreasing a ranking of a route of the extracted plurality of routes for which the number of useable device candidates extracted is zero; and
- outputting the extracted plurality of routes and the assigned rankings to the extracted plurality of routes using the calculated route scores and the calculated patient scores and a result of the extraction of the useable device candidates.

7. The non-transitory computer readable recording medium according to claim 6, comprising:
- adjusting the rankings assigned to the plurality of routes extracted on a basis of the result of extraction of the useable device candidates.

8. The non-transitory computer readable recording medium according to claim 6, further comprising:
- calculating lengths of the plurality of routes extracted and bending degrees of the plurality of routes on a basis of the image information on the inside of the living body of the target patient; and
- calculating the route scores using the calculated lengths of the plurality of routes and the calculated bending degrees of the plurality of routes.

9. The non-transitory computer readable recording medium according to claim 6, comprising:
- calculating invasion degrees of the plurality of routes extracted; and
- calculating the patient scores using the calculated invasion degrees of the plurality of routes.

10. The non-transitory computer readable recording medium according to claim 6, further comprising:
- obtaining patient information related to a characteristic of the target patient; and
- calculating the patient scores on a basis of the patient information.

11. A method of assisting in selecting a route of a living body lumen for delivering a medical instrument to a site within a living body via the living body lumen via an introduction site, the method comprising:
- receiving an input of site information specifying a target site within the living body as a target of delivering the medical instrument and a plurality of introduction sites and an input of procedure information specifying a kind of procedure to be performed by delivering the medical instrument to the target site via the living body lumen;
- obtaining image information on an inside of the living body of a target patient as the target of delivering the medical instrument from the plurality of introduction sites;
- extracting a plurality of routes of the living body lumen, the plurality of routes allowing the medical instrument to be delivered to the target site from the plurality of introduction sites, on a basis of the obtained image information;
- assigning rankings to the extracted plurality of routes by using route scores determined according to ease of delivery of the medical instrument at a time of delivery of the medical instrument via the plurality of routes and patient scores determined according to magnitude of a burden imposed on the target patient;
- extracting medical instruments used for the procedure specified by the procedure information;
- extracting useable device candidates for the medical instruments extracted for the procedure specified by the procedure information, the useable device candidates being available for the procedure specified by the procedure information and in a case where there are no useable device candidates, a number of the useable device candidates extracted is zero;
- decreasing a ranking of a route of the extracted plurality of routes for which the number of useable device candidates extracted is zero; and
- outputting the extracted plurality of routes and the assigned rankings to the extracted plurality of routes using the calculated route scores and the calculated patient scores and a result of the extraction of the useable device candidates.

12. The method according to claim 11, comprising:
- adjusting the rankings assigned to the plurality of routes extracted on a basis of the result of extraction of the useable device candidates.

13. The method according to claim 11, further comprising:
- calculating lengths of the plurality of routes extracted and bending degrees of the plurality of routes on a basis of the image information on the inside of the living body of the target patient; and
- calculating the route scores using the calculated lengths of the plurality of routes and the calculated bending degrees of the plurality of routes.

14. The method according to claim 11, comprising:
- calculating invasion degrees of the plurality of routes extracted; and
- calculating the patient scores using the calculated invasion degrees of the plurality of routes.

15. The method according to claim 11, further comprising:
- obtaining patient information related to a characteristic of the target patient; and calculating the patient scores on a basis of the patient information.

16. A diagnosis method for diagnosing a route of a living body lumen for delivering a medical instrument to a site within a living body via the living body lumen via an introduction site, the diagnosis method comprising:
  receiving an input of site information specifying a target site within the living body as a target of delivering the medical instrument and a plurality of introduction sites and an input of procedure information specifying a kind of procedure to be performed by delivering the medical instrument to the target site via the living body lumen;
  obtaining image information on an inside of the living body of a target patient as the target of delivering the medical instrument from the plurality of introduction sites;
  extracting a plurality of routes of the living body lumen, the plurality of routes allowing the medical instrument to be delivered to the target site from the plurality of introduction sites, on a basis of the obtained image information;
  assigning rankings to the extracted plurality of routes by using route scores determined according to ease of delivery of the medical instrument at a time of delivery of the medical instrument via the plurality of routes and patient scores determined according to magnitude of a burden imposed on the target patient;
  extracting medical instruments used for the procedure specified by the procedure information;
  extracting useable device candidates for the medical instruments extracted for the procedure specified by the procedure information, the useable device candidates being available for the procedure specified by the procedure information and in a case where there are no useable device candidates, a number of the useable device candidates extracted is zero;
  decreasing a ranking of a route of the extracted plurality of routes for which the number of useable device candidates extracted is zero;
  diagnosing the route from the extracted plurality of routes and the assigned rankings to the extracted plurality of routes using the route scores and the patient scores; and
  outputting a result of the extraction of the useable device candidates.

17. The method according to claim 16, further comprising:
  adjusting the rankings assigned to the plurality of routes extracted on a basis of the result of extraction of the useable device candidates.

* * * * *